Jan. 1, 1957 R. L. BYRUM Plant Pat. 1,546
ROSE PLANT
Filed Feb. 21, 1956
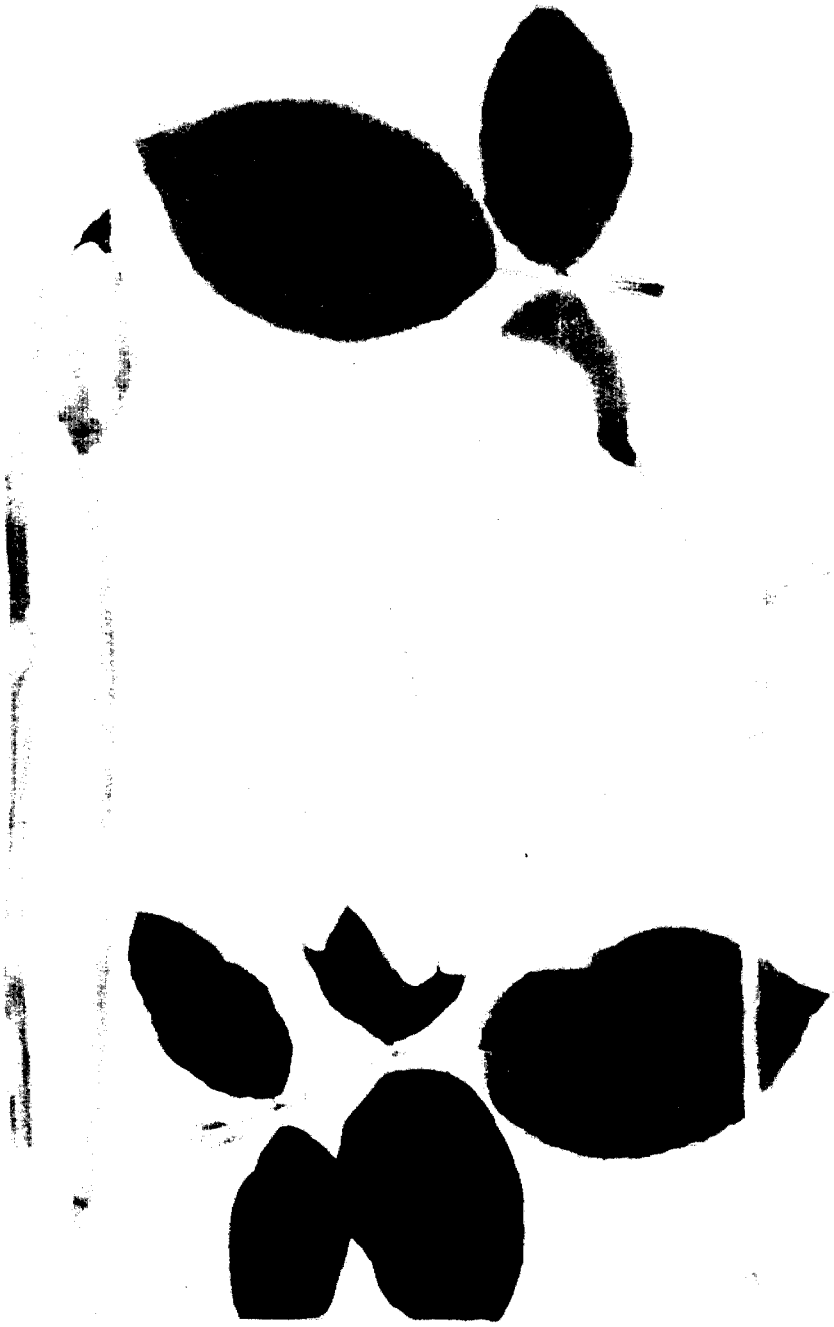
Inventor.
R. L. Byrum
By: Robb & Robb
Attorneys.

United States Patent Office

Plant Pat. 1,546
Patented Jan. 1, 1957

1,546

ROSE PLANT

Roy L. Byrum, Richmond, Ind., assignor to Joseph H. Hill Company, Richmond, Ind., a corporation of Indiana Application February 21, 1956, Serial No. 567,041

1 Claim. (Cl. 47—61)

The present invention relates to a new and distinct variety of rose plant of the hybrid tea class, which was originated by me by crossing an unnamed and unpatented seedling, identified in my breeding records as #40/43, with the unpatented variety "Golden Rapture."

The primary objective in making this cross was to produce a new rose variety having the good qualities of each parent, while eliminating the undesirable qualities of the parents. This objective was fully achieved, as evidenced by the fact that the unnamed variety is normally characterized by its very large flowers which have good keeping qualities that are desirable for a cut flower forcing variety, its blooms develop extra well in water and are of a desirable clear Yellow color, but the plants very often are stunted in growth, whereas the parent variety "Golden Rapture" is notable as a good greenhouse forcing variety and the cut flowers have exceptionally good keeping qualities, but the plants produce numerous weak stems which reduce the number of blooms, and at certain seasons, many blooms are very light in color, being almost White.

My new variety, on the other hand, is most notably characterized by the following outstanding features:

(1) Its strong and vigorous growth;
(2) Its strong stems;
(3) Its long buds in the cutting stage;
(4) The large size of its blooms when open;
(5) Its habit of producing relatively few "work roses" which have defects such as off-colors, crooked stems, deformed outside petals and the like which make them undesirable for bouquets, but which can be used in certain types of "make-up" work with a little "repair";
(6) The distinctive and good Yellow color of its flowers, and their ability to hold the color during all seasons without being affected by hot or cold weather; and
(7) The good keeping qualities of the blooms.

The foregoing characteristics and distinctions definitely differentiate my new variety from its parents, as well as from all other varieties of its class of which I am aware, and asexual reproduction of the new variety by grafting, as performed at Richmond, Indiana, as well as by budding, as performed in Texas, show that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Koster's Color Guide (hereinafter abbreviated as "Koster"), as indicated:

Type: Bush; seedling.
Class: Hybrid tea.

Parentage:
*Seed parent.*—An unnamed seedling designated as #40/43.
*Pollen parent.*—"Golden Rapture."

Propagation: Holds its distinguishing characteristics through succeeding propagations by both grafting and budding.

FLOWER

Locality where grown and observed: Richmond, Indiana.
Flowers borne: Usually one to a stem; on strong stems of medium length.
Quantity of bloom: Abundant in greenhouse.
Continuity: Continuous.
Fragrance: Slight. Nature—tea.

Bud:
*Peduncle.*—Medium length; medium diameter; strong; erect.
*Bark.*—Smooth. Color—Scheeles Green, Plate 860/1 (Wilson).
*Thorns.*—None.
*Prickles.*—Numerous. Color—Uranium Green, Plate 63/3 (Wilson).
*Hairs.*—Few. Color—Uranium Green, Plate 63/3 (Wilson).
*Before calyx breaks.*—Size—medium large. Form—long pointed—ovoid; with a conspicuous neck; with foliaceous appendages on the surface of the bud; with foliaceous parts extending beyond the tip of the bud equal to ¼ or more of its length. Color—Scheeles Green, Plate 860/3 (Wilson).
*As calyx breaks.*—Color (outside of petal)—Lemon Yellow, Plate 4/1 (Wilson).
*As first petal opens.*—Size—medium large. Form—long pointed. Color: Outside—from Lemon Yellow, Plate 4/1 (Wilson) to Lemon Yellow, Plate 4/2 (Wilson); inside—Lemon Yellow, Plate 4/1 (Wilson).
*Opening.*—Opens up well in greenhouse; affected normally by weather conditions, but without unusual characteristics.

Bloom:
*Size (when fully open).*—Large; from 3½ inches to 4 inches.
*Petalage.*—Very double (many petals, usually with no stamens showing); from 45 to 50 petals; arranged irregularly.
*Form.*—High-centered at first, but becoming open; petals being at first tightly rolled outward, but becoming loosely rolled outward later at maturity.

Petals:
*Texture.*—Moderately thick; with both inside and outside satiny.
*Shape.*—Outside petals.—obovate, with apex obtuse. Intermediate petals—obovate, with apex obtuse. Inside petals—spatulate, with apex obtuse.

This description of a newly opened flower was made from a rose grown in a greenhouse in the month of June, at Richmond, Indiana:

*Color.*—Outer petal: Outside surface—Aureolin, Plate 3/2 (Wilson); inside surface—Aureolin, Plate 3/2 (Wilson) at base of petal, gradually changing to Aureolin, Plate 3/3 (Wilson) at tip of petal. Intermediate petal: Outside surface—Mimosa Yellow, Plate 602/1 (Wilson) at base of petal, gradually changing to Mimosa Yellow, Plate 602/2 (Wilson) at tip of petal; inside surface—Mimosa Yellow, Plate 602/1 (Wilson) at base of petal, gradually changing to Mimosa Yellow, Plate 602/2 (Wilson) at tip of petal. Inner petal: Outside surface—Mimosa Yellow, Plate 602/1 (Wilson) at base of petal, gradually changing to Mimosa Yellow, Plate 602/2 (Wilson) at tip of petal; inside surface—Mimosa Yellow, Plate 602/1 (Wilson) at base of petal, gradually changing to Mimosa Yellow, Plate 602/2 (Wilson) at tip of petal.

This description was made from a rose that was open for 3 days in a greenhouse in the month of June, at Richmond, Indiana:

*Color.*—Outer petal: Outside surface—Mimosa Yellow, Plate 602/3 (Wilson), with base of Mimosa Yellow, Plate 602/2 (Wilson); inside surface—Mimosa Yellow, Plate 602/3 (Wilson), with base of Mimosa Yellow, Plate 602/2 (Wilson). Intermediate petal: Outside surface—Mimosa Yellow, Plate 602/3 (Wilson), with base of Mimosa Yellow, Plate 602/2 (Wilson); inside surface—Mimosa Yellow, Plate 602/3 (Wilson), with base of Mimosa Yellow, Plate 602/2 (Wilson). Inner petal: Outside surface—Mimosa Yellow, Plate 602/3 (Wilson), with base of Mimosa Yellow, Plate 602/2 (Wilson); inside surface—Mimosa Yellow, Plate 602/3 (Wilson), with base of Mimosa Yellow, Plate 602/2 (Wilson).

*General color effect.*—Newly opened flower—Aureolin, Plate 3/2 (Wilson). 3-days open—Mimosa Yellow, Plate 602/3 (Wilson).

*Behavior.*—Persist in greenhouse; affected normally by weather conditions, but without unusual characteristics; fading to slightly lighter than Mimosa Yellow, Plate 602/3 (Wilson).

*Flower longevity.*—Cut roses grown in greenhouse and kept at living room temperatures—4 or 5 days in March.

REPRODUCTIVE ORGANS

Stamens: Many; arranged irregularly about pistils; some mixed with petaloids.

Filaments: Short; few with anthers. Color—Aureolin, Plate 3/3 (Wilson).

Anthers: Small; all open at once. Color—Aureolin, Plate 3/2 (Wilson).

Pollen: Sparse. Color—Aureolin, Plate 3/2 (Wilson).

Pistils: Medium number.

Styles: Uneven; medium length; thin; bunched. Color—Uranium Green, Plate 63/3 (Wilson).

Stigma: Color—Pure White, Plate #1 (Koster).

Ovularies: Most all encased in calyx, but some protruding from calyx.

Hips: None.

Sepals: Permanent; medium length; spear-shaped; curled. Color: Inside—Scheeles Green, Plate 860/3 (Wilson), overlaid with White fuzz; outside—Scheeles Green, Plate 860/1 (Wilson), with some shades of Scheeles Green, Plate 860/3 (Wilson) mixed therein.

Seeds: None.

PLANT

Foliage:

*Leaves.*—Compound of 3 to 5 leaflets; abundant; medium large; moderately wrinkled; leathery.

*Leaflets.*—Shape—ovoid. Apex—acute. Base—round. Margin—simply serrate.

*Color.*—Mature: Upper surface—near Holly Green, Plate #82 (Koster); under surface—near Apple Green, Plate #77 (Koster). Young: Upper surface—Lettuce Green, Plate #74 (Koster), with edges and some small veins of near Magenta, Plate #50 (Koster); under surface—Lettuce Green, Plate #74 (Koster), washed or overlaid with Magenta, Plate #50 (Koster).

*Rachis (the supporting stem of the compound leaf).*—Medium heavy. Upper side—grooved. Under side—smooth; prickly.

*Stipules.*—Medium length; medium width; with short points turning out at an angle of less than 45°.

Growth:

*Habit.*—Bush; upright; much-branched.

*Growth.*—Free; vigorous.

*Canes.*—Medium diameter.

*Main stems.*—Color—near Maroon, Plate #97 (Koster). Thorns—several; medium length; hooked downward; with long, narrow base. Color—Bistre, Plate #93 (Koster). Prickles—Few; color—Bistre, Plate #93 (Koster). Hairs—none.

*Branches.*—Color—Spinach Green, Plate 0960/1 (Wilson). Thorns—several; medium length; hooked downward; with long, narrow base. Color—Spinel Red, Plate 0023/2 (Wilson) at base, gradually changing to Uranium Green, Plate 63/3 (Wilson) at tip. Prickles—several; color—Uranium Green, Plate 63/3 (Wilson). Hairs—few; color—Uranium Green, Plate 63/3 (Wilson).

*New shoots.*—Color—Fern Green, Plate 0862/2 (Wilson). Thorns—several; medium length; hooked downward; with long, narrow base. Color—near Spiraea Red, plate 025/2 (Wilson). Prickles—none. Hairs—none.

I claim:

A new and distinct variety of rose plant of the hybrid tea class, substantially as herein shown and described, characterized particularly as to novelty by its strong and vigorous growth, its strong stems, its long buds in the cutting stage, the large size of its flowers when open, its production of relatively few "work roses," the distinctive and good yellow color of its blooms and their ability to hold the color during all seasons without being affected by hot or cold weather, and the good keeping qualities of the blooms.

No references cited.